United States Patent
Ha

(10) Patent No.: US 11,607,445 B2
(45) Date of Patent: Mar. 21, 2023

(54) PHARMACEUTICAL COMPOSITION FOR PREVENTING OR TREATING DIABETIC COMPLICATIONS

(71) Applicant: Amolifescience Co., Ltd., Seoul (KR)

(72) Inventor: Kwon-Soo Ha, Chuncheon-si (KR)

(73) Assignee: Amolifescience Co., Ltd., Seoul (KR)

( * ) Notice: Subject to any disclaimer, the term of this patent is extended or adjusted under 35 U.S.C. 154(b) by 0 days.

(21) Appl. No.: 16/823,493

(22) Filed: Mar. 19, 2020

(65) Prior Publication Data

US 2020/0360486 A1    Nov. 19, 2020

(30) Foreign Application Priority Data

May 14, 2019 (KR) .................. 10-2019-0056598
Sep. 19, 2019 (KR) .................. 10-2019-0115545

(51) Int. Cl.
*A61K 38/28* (2006.01)
*A61P 3/10* (2006.01)
*A61K 38/39* (2006.01)

(52) U.S. Cl.
CPC .............. *A61K 38/28* (2013.01); *A61K 38/39* (2013.01); *A61P 3/10* (2018.01)

(58) Field of Classification Search
CPC ................................ A61K 38/28; A61K 38/39
See application file for complete search history.

(56) References Cited

U.S. PATENT DOCUMENTS

| 6,533,819 B1 | 3/2003 | Urry et al. |
| 2013/0150291 A1 | 6/2013 | Jowett et al. |
| 2014/0128323 A1 | 5/2014 | Ha et al. |
| 2018/0002700 A1 | 1/2018 | Ha et al. |

FOREIGN PATENT DOCUMENTS

| KR | 876657 B1 * | 1/2008 |
| KR | 20130115086 A | 10/2013 |
| KR | 10-2014-0103985 A | 8/2014 |
| KR | 10-2017-0128058 A | 11/2017 |
| WO | WO 2009/158704 A2 | 12/2009 |
| WO | WO 2011/146518 A1 | 11/2011 |
| WO | WO 2013/082116 A1 | 6/2013 |

OTHER PUBLICATIONS

Wahren et al., Am. J. Physiol. Endocr. Metab. 278: E759-768, (2000).*
MacEwan and Chilkoti, J. of controlled release, 190: 314-330, (2014).*
Extended European Search Report for Application No. EP 20174114.7 dated Oct. 19, 2020.
Jung et al., Preventive Effects of Thermosensitive Biopolymer-Conjugated C-Peptide against High Glucose-Induced Endothelial Cell Dysfunction. Macromol Biosci. Sep. 2019;19(9):e1900129. doi: 10.1002/mabi.201900129. Epub Jul. 16, 2019.
Lee et al. Application of elastin-like biopolymer-conjugated C-peptide hydrogel for systemic long-term delivery against diabetic aortic dysfunction. Acta Biomater. Dec. 2020;118:32-43. doi: 10.1016/j.actbio.2020.09.055. Epub Oct. 6, 2020.
MacEwan et al., Applications of elastin-like polypeptides in drug delivery. J Control Release. Sep. 28, 2014;190:314-30. doi: 10.1016/j.jconrel.2014.06.028. Epub Jun. 28, 2014.
Wahren et al., Role of C-peptide in human physiology. Am J Physiol Endocrinol Metab. May 2000;278(5):E759-68.

* cited by examiner

Primary Examiner — Gyan Chandra
(74) Attorney, Agent, or Firm — Wolf, Greenfield & Sacks, P.C.

(57) ABSTRACT

Disclosed is a composition and a method for the prevention or treatment of diabetic complications, which includes C-peptide bound to elastin-like polypeptide (ELP) and is thus capable of effectively preventing or treating diseases resulting from hyperglycemia, which is a major cause of diabetes, for example, diabetic retinopathy, and the like.

7 Claims, 14 Drawing Sheets

Specification includes a Sequence Listing.

| ELP analogues | Amino acid sequence |
|---|---|
| K8 | [(VPGVG)$_{11}$(VPGKG)$_1$(VPGVG)$_1$]$_8$ |
| K9-C-peptide | [(VPGVG)$_{11}$(VPGKG)$_1$(VPGVG)$_1$]$_9$DPNYPRGHEAEDLQVGQVELGGGPGAGSLQPLALEGSLQ |

Elastin unit, VPGVG; lysine-substituted elastin unit, (VPGKG); linker, DPNYPRGH;
C-peptide sequence, EAEDLQVGQVELGGGPGAGSLQPLALEGSLQ

SEQUENCE LISTING

<160> NUMBER OF SEQ ID NOS: 9

<210> SEQ ID NO 1
<211> LENGTH: 5
<212> TYPE: PRT
<213> ORGANISM: Artificial Sequence
<220> FEATURE:
<223> OTHER INFORMATION: elastin-like polypeptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 1

```
Val Pro Gly Xaa Gly
1               5
```

<210> SEQ ID NO 2
<211> LENGTH: 65
<212> TYPE: PRT
<213> ORGANISM: Artificial Sequence
<220> FEATURE:
<223> OTHER INFORMATION: elastin-like polypeptides

<400> SEQUENCE: 2

```
Val Pro Gly Val Gly Val Pro Gly Val Gly Val Pro Gly Val Gly Val
1               5                   10                  15

Pro Gly Val Gly Val Pro Gly Val Gly Val Pro Gly Val Gly Val Pro
                20                  25                  30

Gly Val Gly Val Pro Gly Val Gly Val Pro Gly Val Gly Val Pro Gly
            35                  40                  45

Val Gly Val Pro Gly Val Gly Val Pro Gly Lys Gly Val Pro Gly Val
        50                  55                  60

Gly
65
```

<210> SEQ ID NO 3
<211> LENGTH: 585
<212> TYPE: PRT
<213> ORGANISM: Artificial Sequence
<220> FEATURE:
<223> OTHER INFORMATION: elastin-like polypeptides

<400> SEQUENCE: 3

```
Val Pro Gly Val Gly Val Pro Gly Val Gly Val Pro Gly Val Gly Val
1               5                   10                  15

Pro Gly Val Gly Val Pro Gly Val Gly Val Pro Gly Val Gly Val Pro
                20                  25                  30

Gly Val Gly Val Pro Gly Val Gly Val Pro Gly Val Gly Val Pro Gly
            35                  40                  45

Val Gly Val Pro Gly Val Gly Val Pro Gly Lys Gly Val Pro Gly Val
        50                  55                  60

Gly Val Pro Gly Val Gly Val Pro Gly Val Gly Val Pro Gly Val Gly
65                  70                  75                  80

Val Pro Gly Val Gly Val Pro Gly Val Gly Val Pro Gly Val Gly Val
                85                  90                  95

Pro Gly Val Gly Val Pro Gly Val Gly Val Pro Gly Val Gly Val Pro
                100                 105                 110

Gly Val Gly Val Pro Gly Val Gly Val Pro Gly Lys Gly Val Pro Gly
            115                 120                 125

Val Gly Val Pro Gly Val Gly Val Pro Gly Val Gly Val Pro Gly Val
        130                 135                 140

Gly Val Pro Gly Val Gly Val Pro Gly Val Gly Val Pro Gly Val Gly
145                 150                 155                 160

Val Pro Gly Val Gly Val Pro Gly Val Gly Val Pro Gly Val Gly Val
                165                 170                 175

Pro Gly Val Gly Val Pro Gly Val Gly Val Pro Gly Lys Gly Val Pro
                180                 185                 190

Gly Val Gly Val Pro Gly Val Gly Val Pro Gly Val Gly Val Pro Gly
            195                 200                 205

Val Gly Val Pro Gly Val Gly Val Pro Gly Val Gly Val Pro Gly Val
```

```
                210                 215                 220
Gly Val Pro Gly Val Gly Val Pro Gly Val Gly Val Pro Val Gly
225                 230                 235                 240

Val Pro Gly Val Gly Val Pro Gly Val Gly Val Pro Gly Lys Gly Val
                245                 250                 255

Pro Gly Val Gly Val Pro Gly Val Gly Val Pro Gly Val Gly Val Pro
                260                 265                 270

Gly Val Gly Val Pro Gly Val Gly Val Pro Gly Val Gly Val Pro Gly
                275                 280                 285

Val Gly Val Pro Gly Val Gly Val Pro Gly Val Gly Val Pro Gly Val
                290                 295                 300

Gly Val Pro Gly Val Gly Val Pro Gly Val Gly Val Pro Gly Lys Gly
305                 310                 315                 320

Val Pro Gly Val Gly Val Pro Gly Val Gly Val Pro Gly Val Gly Val
                325                 330                 335

Pro Gly Val Gly Val Pro Gly Val Gly Val Pro Gly Val Gly Val Pro
                340                 345                 350

Gly Val Gly Val Pro Gly Val Gly Val Pro Gly Val Gly Val Pro Gly
                355                 360                 365

Val Gly Val Pro Gly Val Gly Val Pro Gly Val Gly Val Pro Gly Lys
                370                 375                 380

Gly Val Pro Gly Val Gly Val Pro Gly Val Gly Val Pro Gly Val Gly
385                 390                 395                 400

Val Pro Gly Val Gly Val Pro Gly Val Gly Val Pro Gly Val Gly Val
                405                 410                 415

Pro Gly Val Gly Val Pro Gly Val Gly Val Pro Gly Val Gly Val Pro
                420                 425                 430

Gly Val Gly Val Pro Gly Val Gly Val Pro Gly Val Gly Val Pro Gly
                435                 440                 445

Lys Gly Val Pro Gly Val Gly Val Pro Gly Val Gly Val Pro Gly Val
                450                 455                 460

Gly Val Pro Gly Val Gly Val Pro Gly Val Gly Val Pro Gly Val Gly
465                 470                 475                 480

Val Pro Gly Val Gly Val Pro Gly Val Gly Val Pro Gly Val Gly Val
                485                 490                 495

Pro Gly Val Gly Val Pro Gly Val Gly Val Pro Gly Val Gly Val Pro
                500                 505                 510

Gly Lys Gly Val Pro Gly Val Gly Val Pro Gly Val Gly Val Pro Gly
                515                 520                 525

Val Gly Val Pro Gly Val Gly Val Pro Gly Val Gly Val Pro Gly Val
                530                 535                 540

Gly Val Pro Gly Val Gly Val Pro Gly Val Gly Val Pro Gly Val Gly
545                 550                 555                 560

Val Pro Gly Val Gly Val Pro Gly Val Gly Val Pro Gly Val Gly Val
                565                 570                 575

Pro Gly Lys Gly Val Pro Gly Val Gly
                580                 585

<210> SEQ ID NO 4
<211> LENGTH: 31
<212> TYPE: PRT
<213> ORGANISM: Homo sapiens

<400> SEQUENCE: 4
```

```
Glu Ala Glu Asp Leu Gln Val Gly Gln Val Glu Leu Gly Gly Gly Pro
1               5                   10                  15

Gly Ala Gly Ser Leu Gln Pro Leu Ala Leu Glu Gly Ser Leu Gln
            20                  25                  30

<210> SEQ ID NO 5
<211> LENGTH: 8
<212> TYPE: PRT
<213> ORGANISM: Artificial Sequence
<220> FEATURE:
<223> OTHER INFORMATION: linker

<400> SEQUENCE: 5

Asp Pro Asn Tyr Pro Arg Gly His
1               5

<210> SEQ ID NO 6
<211> LENGTH: 520
<212> TYPE: PRT
<213> ORGANISM: Artificial Sequence
<220> FEATURE:
<223> OTHER INFORMATION: Synthetic

<400> SEQUENCE: 6

Val Pro Gly Val Gly Val Pro Gly Val Gly Val Pro Gly Val Gly Val
1               5                   10                  15

Pro Gly Val Gly Val Pro Gly Val Gly Val Pro Gly Val Gly Val Pro
            20                  25                  30

Gly Val Gly Val Pro Gly Val Gly Val Pro Gly Val Gly Val Pro Gly
        35                  40                  45

Val Gly Val Pro Gly Val Gly Val Pro Gly Lys Gly Val Pro Gly Val
    50                  55                  60

Gly Val Pro Gly Val Gly Val Pro Gly Val Gly Val Pro Gly Val Gly
65                  70                  75                  80

Val Pro Gly Val Gly Val Pro Gly Val Gly Val Pro Gly Val Gly Val
                85                  90                  95

Pro Gly Val Gly Val Pro Gly Val Gly Val Pro Gly Val Gly Val Pro
            100                 105                 110

Gly Val Gly Val Pro Gly Val Gly Val Pro Gly Lys Gly Val Pro Gly
        115                 120                 125

Val Gly Val Pro Gly Val Gly Val Pro Gly Val Gly Val Pro Gly Val
    130                 135                 140

Gly Val Pro Gly Val Gly Val Pro Gly Val Gly Val Pro Gly Val Gly
145                 150                 155                 160

Val Pro Gly Val Gly Val Pro Gly Val Gly Val Pro Gly Val Gly Val
                165                 170                 175

Pro Gly Val Gly Val Pro Gly Val Gly Val Pro Gly Lys Gly Val Pro
            180                 185                 190

Gly Val Gly Val Pro Gly Val Gly Val Pro Gly Val Gly Val Pro Gly
        195                 200                 205

Val Gly Val Pro Gly Val Gly Val Pro Gly Val Gly Val Pro Gly Val
    210                 215                 220

Gly Val Pro Gly Val Gly Val Pro Gly Val Gly Val Pro Gly Val Gly
225                 230                 235                 240

Val Pro Gly Val Gly Val Pro Gly Val Gly Val Pro Gly Lys Gly Val
                245                 250                 255

Pro Gly Val Gly Val Pro Gly Val Gly Val Pro Gly Val Gly Val Pro
            260                 265                 270
```

Gly Val Gly Val Pro Gly Val Gly Val Pro Gly Val Gly Val Pro Gly
            275                 280                 285

Val Gly Val Pro Gly Val Gly Val Pro Gly Val Gly Val Pro Gly Val
        290                 295                 300

Gly Val Pro Gly Val Gly Val Pro Gly Val Gly Val Pro Gly Lys Gly
305                 310                 315                 320

Val Pro Gly Val Gly Val Pro Gly Val Gly Val Pro Gly Val Gly Val
            325                 330                 335

Pro Gly Val Gly Val Pro Gly Val Gly Val Pro Gly Val Gly Val Pro
        340                 345                 350

Gly Val Gly Val Pro Gly Val Gly Val Pro Gly Val Gly Val Pro Gly
            355                 360                 365

Val Gly Val Pro Gly Val Gly Val Pro Gly Val Gly Val Pro Gly Lys
        370                 375                 380

Gly Val Pro Gly Val Gly Val Pro Gly Val Gly Val Pro Gly Val Gly
385                 390                 395                 400

Val Pro Gly Val Gly Val Pro Gly Val Gly Val Pro Gly Val Gly Val
            405                 410                 415

Pro Gly Val Gly Val Pro Gly Val Gly Val Pro Gly Val Gly Val Pro
        420                 425                 430

Gly Val Gly Val Pro Gly Val Gly Val Pro Gly Val Gly Val Pro Gly
            435                 440                 445

Lys Gly Val Pro Gly Val Gly Val Pro Gly Val Gly Val Pro Gly Val
        450                 455                 460

Gly Val Pro Gly Val Gly Val Pro Gly Val Gly Val Pro Gly Val Gly
465                 470                 475                 480

Val Pro Gly Val Gly Val Pro Gly Val Gly Val Pro Gly Val Gly Val
            485                 490                 495

Pro Gly Val Gly Val Pro Gly Val Gly Val Pro Gly Val Gly Val Pro
        500                 505                 510

Gly Lys Gly Val Pro Gly Val Gly
        515                 520

<210> SEQ ID NO 7
<211> LENGTH: 624
<212> TYPE: PRT
<213> ORGANISM: Artificial Sequence
<220> FEATURE:
<223> OTHER INFORMATION: Synthetic

<400> SEQUENCE: 7

Val Pro Gly Val Gly Val Pro Gly Val Gly Val Pro Gly Val Gly Val
1               5                   10                  15

Pro Gly Val Gly Val Pro Gly Val Gly Val Pro Gly Val Gly Val Pro
            20                  25                  30

Gly Val Gly Val Pro Gly Val Gly Val Pro Gly Val Gly Val Pro Gly
        35                  40                  45

Val Gly Val Pro Gly Val Gly Val Pro Gly Lys Gly Val Pro Gly Val
    50                  55                  60

Gly Val Pro Gly Val Gly Val Pro Gly Val Gly Val Pro Gly Val Gly
65                  70                  75                  80

Val Pro Gly Val Gly Val Pro Gly Val Gly Val Pro Gly Val Gly Val
            85                  90                  95

Pro Gly Val Gly Val Pro Gly Val Gly Val Pro Gly Val Gly Val Pro
        100                 105                 110

-continued

Gly Val Gly Val Pro Gly Val Gly Val Pro Gly Lys Gly Val Pro Gly
            115                 120                 125
Val Gly Val Pro Gly Val Gly Val Pro Gly Val Gly Val Pro Gly Val
        130                 135                 140
Gly Val Pro Gly Val Gly Val Pro Gly Val Gly Val Pro Gly Val Gly
145                 150                 155                 160
Val Pro Gly Val Gly Val Pro Gly Val Gly Val Pro Gly Val Gly Val
                165                 170                 175
Pro Gly Val Gly Val Pro Gly Val Gly Val Pro Gly Lys Gly Val Pro
            180                 185                 190
Gly Val Gly Val Pro Gly Val Gly Val Pro Gly Val Gly Val Pro Gly
        195                 200                 205
Val Gly Val Pro Gly Val Gly Val Pro Gly Val Gly Val Pro Gly Val
    210                 215                 220
Gly Val Pro Gly Val Gly Val Pro Gly Val Gly Val Pro Gly Val Gly
225                 230                 235                 240
Val Pro Gly Val Gly Val Pro Gly Val Gly Val Pro Gly Lys Gly Val
                245                 250                 255
Pro Gly Val Gly Val Pro Gly Val Gly Val Pro Gly Val Gly Val Pro
            260                 265                 270
Gly Val Gly Val Pro Gly Val Gly Val Pro Gly Val Gly Val Pro Gly
        275                 280                 285
Val Gly Val Pro Gly Val Gly Val Pro Gly Val Gly Val Pro Gly Val
    290                 295                 300
Gly Val Pro Gly Val Gly Val Pro Gly Val Gly Val Pro Gly Lys Gly
305                 310                 315                 320
Val Pro Gly Val Gly Val Pro Gly Val Gly Val Pro Gly Val Gly Val
                325                 330                 335
Pro Gly Val Gly Val Pro Gly Val Gly Val Pro Gly Val Gly Val Pro
            340                 345                 350
Gly Val Gly Val Pro Gly Val Gly Val Pro Gly Val Gly Val Pro Gly
        355                 360                 365
Val Gly Val Pro Gly Val Gly Val Pro Gly Val Gly Val Pro Gly Lys
    370                 375                 380
Gly Val Pro Gly Val Gly Val Pro Gly Val Gly Val Pro Gly Val Gly
385                 390                 395                 400
Val Pro Gly Val Gly Val Pro Gly Val Gly Val Pro Gly Val Gly Val
                405                 410                 415
Pro Gly Val Gly Val Pro Gly Val Gly Val Pro Gly Val Gly Val Pro
            420                 425                 430
Gly Val Gly Val Pro Gly Val Gly Val Pro Gly Val Gly Val Pro Gly
        435                 440                 445
Lys Gly Val Pro Gly Val Gly Val Pro Gly Val Gly Val Pro Gly Val
    450                 455                 460
Gly Val Pro Gly Val Gly Val Pro Gly Val Gly Val Pro Gly Val Gly
465                 470                 475                 480
Val Pro Gly Val Gly Val Pro Gly Val Gly Val Pro Gly Val Gly Val
                485                 490                 495
Pro Gly Val Gly Val Pro Gly Val Gly Val Pro Gly Val Gly Val Pro
            500                 505                 510
Gly Lys Gly Val Pro Gly Val Gly Val Pro Gly Val Gly Val Pro Gly
        515                 520                 525

```
Val Gly Val Pro Gly Val Gly Val Pro Gly Val Gly Val Pro Gly Val
        530                 535                 540
Gly Val Pro Gly Val Gly Val Pro Gly Val Gly Val Pro Gly Val Gly
545                 550                 555                 560
Val Pro Gly Val Gly Val Pro Gly Val Gly Val Pro Gly Val Gly Val
                565                 570                 575
Pro Gly Lys Gly Val Pro Gly Val Gly Asp Pro Asn Tyr Pro Arg Gly
            580                 585                 590
His Glu Ala Glu Asp Leu Gln Val Gly Gln Val Glu Leu Gly Gly Gly
            595                 600                 605
Pro Gly Ala Gly Ser Leu Gln Pro Leu Ala Leu Glu Gly Ser Leu Gln
    610                 615                 620

<210> SEQ ID NO 8
<211> LENGTH: 5
<212> TYPE: PRT
<213> ORGANISM: Artificial Sequence
<220> FEATURE:
<223> OTHER INFORMATION: Synthetic

<400> SEQUENCE: 8

Val Pro Gly Val Gly
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic

<400> SEQUENCE: 9

Val Pro Gly Lys Gly
1               5
```

PHARMACEUTICAL COMPOSITION FOR PREVENTING OR TREATING DIABETIC COMPLICATIONS

CROSS REFERENCE TO RELATED APPLICATIONS

This application claims the benefit of Korean Patent Application Nos. KR 10-2019-0056598 and KR 10-2019-0115545, which are each hereby incorporated by reference in their entireties into this application.

SEQUENCE LISTING

The instant application contains a Sequence Listing which has been submitted in ASCII format via EFS-Web and is hereby incorporated by reference in its entirety. Said ASCII copy, created on Aug. 25, 2021, is named A125370001US00-SUBSEQ-TC and is 17,164 bytes in size.

BACKGROUND

1. Technical Field

The present disclosure relates to pharmaceutical compositions and methods for the prevention or treatment of diabetic complications, and more particularly to pharmaceutical compositions for the prevention or treatment of diabetic complications, which includes C-peptide bound to a temperature-sensitive biopolymer (elastin-like polypeptide).

2. Description of the Related Art

Diabetes refers to metabolic disorders that have multiple etiologies and are characterized by chronic hyperglycemia caused by deficient insulin secretion or deficient insulin action. When blood glucose levels are abnormally high for a long time, various complications occur because of chronic metabolic disorders and chronic blood vessel damage due thereto.

Based on recent study reports, diabetic angiopathy is caused by apoptosis due to an increase in intracellular reactive oxygen species (ROS) levels and the activation of transglutaminase 2 (TGase 2).

Conventional treatment of diabetic complications due to chronic hyperglycemia has been achieved through a passive form of therapy that regulates blood sugar by administering hypoglycemia-inducing drugs such as insulin and the like. However, there are certain limitations on the prevention and treatment of long-term diabetic complications using blood sugar control alone.

Recently, C-peptide has been reported to be effective in the treatment and prevention of diabetic angiopathy, including diabetic retinopathy, neuropathy, nephropathy, cardiovascular disease, wound-healing delay, and the like. Accordingly, C-peptide has emerged as a prominent potential drug for treating diabetic complications. However, C-peptide has a short half-life when injected in vivo, which makes it necessary to repeatedly inject drugs or implant a device such as an osmotic pump. In addition, since the production of C-peptide is dependent on chemical synthesis, there is a problem of high cost due to continuous injection.

In regard thereto, Korean Patent Application Publication No. 10-2013-0115086 discloses a pegylated C-peptide including a PEG moiety covalently attached to the N-terminus of the C-peptide in order to improve the half-life of the C-peptide. However, long-term circulation of PEG molecules may induce an immune response or the like, and moreover, due to the polydispersity of polymers and poor stoichiometry, it is not possible to control the in-vivo behavior of the conjugate.

SUMMARY

Some aspects of the present disclosure are to provide: a pharmaceutical composition for the effective prevention or treatment of diabetic complications caused by hyperglycemia; and a method for preventing or treating diabetic complications comprising: administering to the subject a pharmaceutical composition comprising an effective amount of C-peptide bound to elastin-like polypeptide (ELP).

In order to accomplish the above, some aspects of the present disclosure provides a pharmaceutical composition and a method for the prevention or treatment of diabetic complications including C-peptide bound to elastin-like polypeptide (ELP).

In some aspects of the present disclosure, the elastin-like polypeptide may comprise at least one of pentapeptide motif VPGXG of SEQ ID NO: 1, and in the pentapeptide motif VPGXG, X is each independently selected from among valine (Val; V) and lysine (Lys; K), at least one of which may include lysine (Lys; K).

The elastin-like polypeptide may include at least one repeating amino acid sequence unit of SEQ ID NO: 2.

The C-peptide may comprise or be composed of the amino acid sequence of SEQ ID NO: 4.

In some aspects of the present disclosure, diabetic complications are caused by vascular leakage, and may include diabetic retinopathy, diabetic stroke, diabetic cardiovascular disease, diabetic kidney disease, diabetic lung disease, diabetic peripheral neuropathy, diabetic wound-healing delay or diabetic cancer metastasis.

In some aspects of the present disclosure, the pharmaceutical composition and the method for the prevention or treatment of diabetic complications is capable of inhibiting apoptosis, an increase in intracellular reactive oxygen species (ROS) levels and transglutaminase 2 (TGase 2) activity.

In some aspects of the present disclosure, the C-peptide bound to the elastin-like polypeptide may have a phase-transition behavior.

According to some aspects of the present disclosure, a pharmaceutical composition and a method for the prevention or treatment of diabetic complications includes C-peptide bound to elastin-like polypeptide (ELP) and can thus effectively prevent and treat diseases caused by hyperglycemia, which is a major cause of diabetes.

Specifically, the compositions and the methods for the prevention or treatment of diabetic complications according to some aspects of the present disclosure are capable of continuously releasing C-peptide for a long time in vivo through a single injection. Moreover, it is possible to significantly reduce production costs compared to a conventional chemical-synthesis-dependent C-peptide production method and also to minimize side effects of existing chemical compounds.

DESCRIPTION OF SPECIFIC EMBODIMENTS

Figures 1A, 1B:
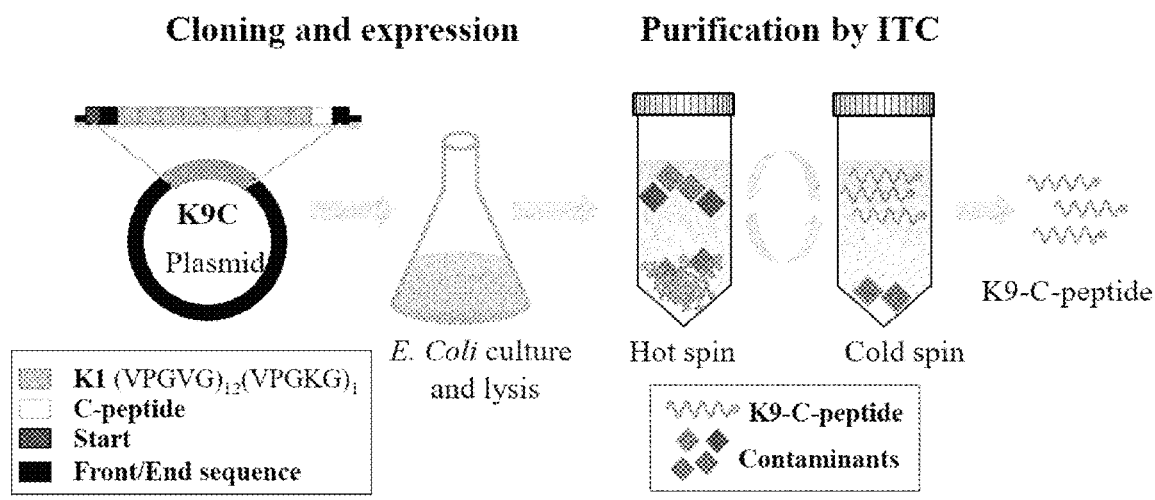
FIGS. 1A, 1B and 1C, respectively, show the K8 and K9-C-peptide sequences according to an embodiment of the present disclosure, the expression and purification cycle of K9-C-peptide, and an agarose gel electrophoresis image of K9-C-peptide (Sequences shown are: K8 (SEQ ID NO: 6), K9-C-peptide (SEQ ID NO: 7), Elastin Unit (SEQ ID NO: 8), Lysin-substituted elastin unit (SEQ ID NO: 9), Linker (SEQ ID NO: 5), C-peptide sequence (SEQ ID NO: 4))

The present disclosure pertains to pharmaceutical compositions and methods for the prevention or treatment of diabetic complications, including C-peptide bound to elastin-like polypeptide (ELP), or therapeutic methods.

The present inventors have designed a novel temperature-sensitive-biopolymer-bound C-peptide formed by binding C-peptide, which is known to be effective in the prevention and treatment of diabetic complications, to the elastin-like polypeptide (ELP) of a temperature-sensitive biopolymer through gene recombination, and have experimentally ascertained that the temperature-sensitive biopolymer-bound C-peptide has the effect of preventing or treating and ameliorating diabetic complications by continuously releasing C-peptide for a long time in vivo through a single injection, thus culminating in the present disclosure.

Hereinafter, a detailed description will be given of the present disclosure.

The pharmaceutical composition and the method for the prevention or treatment of diabetic complications according to some aspects of the present disclosure includes C-peptide bound to elastin-like polypeptide (ELP), thereby suppressing the generation of reactive oxygen species (ROS) and activation of transglutaminase 2 (TGase2) resulting from hyperglycemia, ultimately preventing hyperglycemia-induced vascular dysfunction due to the inhibition of endothelial cell death, as can be experimentally confirmed.

In some aspects of the present disclosure, in order to enable continuous release and transfer of C-peptide drugs in vivo for a long time, a gene that expresses C-peptide and a temperature-sensitive biopolymer called elastin-like polypeptide (ELP) in the state of being bound to each other may be cloned through genetic engineering, expressed in E. coli, isolated, and effectively applied to the prevention and treatment of diabetic complications.

The elastin-like polypeptide (ELP), which is sensitive to heat, is a kind of recombinant biopolymer useful for drug delivery. The elastin-like polypeptide (ELP) is composed of repeated pentapeptide motifs.

In some aspects of the present disclosure, the elastin-like polypeptide comprises SEQ ID NO: 1 of VPGXG, which is the repeating pentapeptide unit.

SEQ ID NO: 1 is VPGXG (Val-Pro-Gly-Xaa-Gly), in which X (or Xaa) is a guest residue.

The elastin-like polypeptide may be represented by the following equation.

$$[\text{SEQ ID NO: 1}]_n \qquad \text{[Equation 1]}$$

Here, n is the number of repetitions of SEQ ID NO: 1, and is an integer of 1 or more, and preferably an integer of 60 to 221.

In the repeated pentapeptide motif VPGXG, X is independently selected from among valine (Val; V) and lysine (Lys; K), at least one of which includes lysine (Lys; K).

As used herein, Val (V), Pro (P), Gly (G), Lys (K) and the like are amino acid abbreviations. Val is the abbreviation for valine, Pro is the abbreviation for proline, Gly is the abbreviation for glycine, and Lys is the abbreviation for lysine. Also, valine is represented as V, proline is represented as P, glycine is represented as G, and lysine is represented as K. These abbreviations are widely used in the art.

According to some aspects of the present disclosure, the elastin-like polypeptide (ELP) is able to form a polypeptide block in which the pentapeptide is repeated.

For example, the elastin-like polypeptide (ELP) is able to form the $[(\text{VPGVG})_{11}(\text{VPGKG})_1(\text{VPGVG})_1]$ repeating amino acid sequence unit of SEQ ID NO: 2.

In some aspects of the present disclosure, the physicochemical properties of elastin-like polypeptide (ELP), such as temperature-sensitive sol-gel transition, enable temporal and spatial control of the release of drugs, whereby the C-peptide bound to the elastin-like polypeptide (ELP) according to some aspects of the present disclosure is capable of continuously releasing C-peptide for a long time in vivo. The temperature that enables the sol-gel transition may be easily adjusted by changing the number and sequence of ELP units, and genetic conjugation of protein or peptide with ELP may be achieved by strictly controlling physicochemical properties and stoichiometry between protein and polymer using recombinant DNA techniques.

For example, the elastin-like polypeptide (ELP) of some aspects of the present disclosure is ELP containing lysine (K) and including at least one $[(\text{VPGVG})_{11}(\text{VPGKG})_1(\text{VPGVG})_1]$ repeating amino acid sequence unit of SEQ ID NO: 2, and preferably includes 5 to 17 $[(\text{VPGVG})_{11}(\text{VPGKG})_1(\text{VPGVG})_1]$ repeating amino acid sequence units of SEQ ID NO: 2.

Some embodiments of the present disclosure may provide the elastin-like polypeptide (ELP) of SEQ ID NO: 3, including 9 repeating amino acid sequence units of SEQ ID NO: 2.

SEQ ID NO: 3 may be composed of $[(\text{VPGVG})_{11}(\text{VPGKG})_1(\text{VPGVG})_1]9$.

In an embodiment of the present disclosure, the C-peptide may comprise or be EAEDLQVGQVELGGGPGAGSLQ-PLALEGSLQ, that is, SEQ ID NO: 4, but is not limited thereto.

SEQ ID NO: 4 may comprise or be composed of Glu-Ala-Glu-Asp-Leu-Gln-Val-Gly-Gln-Val-Glu-Leu-Gly-Gly-Gly-Pro-Gly-Ala-Gly-Ser-Leu-Gln-Pro-Leu-Ala-Leu-Glu-Gly-Ser-Leu-Gln.

As used herein, the C-peptide bound to the elastin-like polypeptide composed of 9 [(VPGVG)$_{11}$(VPGKG)$_{1}$(VPGVG)$_{1}$] repeating amino acid sequence units of SEQ ID NO: 2 may be referred to as "K9-C-peptide".

In some embodiments, binding of ELP and C-peptide may be carried out through an additional linker, and ELP and C-peptide may be bound to each other by a linker.

The linker includes the amino acid sequence of DPNY-PRGH (Asp-Pro-Asn-Tyr-Pro-Arg-Gly-His) of SEQ ID NO: 5.

In the pharmaceutical composition and the method for the prevention or treatment of diabetic complications according to an embodiment of the present disclosure, the C-peptide bound to the elastin-like polypeptide, for example, K9-C-peptide, enables sol-gel transition at a temperature equal to or lower than body temperature, and may have a phase-transition behavior.

The pharmaceutical composition and the method for the prevention or treatment of diabetic complications according to some aspects of the present disclosure includes the C-peptide bound to the elastin-like polypeptide (ELP), and may thus continuously release C-peptide for a long time through phase transition using a single injection, thereby effectively preventing or treating diabetic complications caused by hyperglycemia.

In particular, when the K9-C-peptide according to some aspects of the present disclosure is injected once, C-peptide having a therapeutic effect on diabetic complications may be released from the K9-C-peptide for 20 days, and maximally 30 days, thereby inhibiting increased intracellular reactive oxygen species (ROS) levels, increased transglutaminase 2 (TGase 2) activity, and apoptosis, caused by hyperglycemia.

The pharmaceutical composition and the method for the prevention or treatment of diabetic complications according to some aspects of the present disclosure may be applied without particular limitation to conditions known as diabetic complications, for example, diabetic complications such as diabetic retinopathy, diabetic stroke, diabetic cardiovascular disease, diabetic kidney disease, diabetic lung disease, diabetic peripheral neuropathy, diabetic wound-healing delay, diabetic cancer metastasis and the like. Among these, the pharmaceutical compositions and the methods of some aspects of the present disclosure may be more effectively applied to diabetic retinopathy, diabetic lung disease, diabetic kidney disease, diabetic wound-healing delay, diabetic cancer metastasis or diabetic cardiovascular disease.

For example, the cardiovascular disease may include hypertension, dyslipidemia, angina pectoris, artery vasospasm, cardiac arrhythmia, cardiac hypertrophy, cerebral infarction, congestive heart failure, arteriosclerosis, coronary heart disease, myocardial infarction, and the like, but is not particularly limited thereto.

The pharmaceutical composition for the prevention or treatment of diabetic complications according to some aspects of the present disclosure may be administered in an effective amount or a pharmaceutically effective amount. Here, the term "effective amount" or "pharmaceutically effective amount" refers to an amount sufficient to have a prophylactic or therapeutic effect on diabetic complications and an amount not causing side effects or serious or excessive immune responses. The effective dose level may vary depending on various factors, including the disorder to be treated, the severity of the disorder, the activity of the specific compound, the route of administration, the rate of elimination, the duration of treatment, drugs used concurrently or in combination therewith, the subject's age, weight, gender, diet and general health, and factors known in the pharmaceutical and medical fields. A variety of general considerations are known to those skilled in the art when determining the "effective amount" or "pharmaceutically effective amount".

Preferably, the pharmaceutical composition and the method for the prevention or treatment of diabetic complications according to some aspects of the present disclosure may be used for at least one of ocular administration, intravitreal injection of the eyes, intraperitoneal injection, subcutaneous injection, intradermal injection, intramuscular injection and patch administration.

The pharmaceutical composition and the method for the prevention or treatment of diabetic complications according to some aspects of the present disclosure may be appropriately administered depending on the disease and weight of a subject.

For example, for the prevention or treatment of diabetic complications in humans using K9-C-peptide, a single dose administered using the intravitreal injection method of an aspect of the present disclosure may range from 1.27 micrograms to 1.27 mg, a single dose administered using the subcutaneous injection method or the intraperitoneal injection method may be 1 mg/kg to 1 g/kg, and a single dose administered using the intradermal injection method may be 41.5 micrograms to 41.5 mg.

Meanwhile, the pharmaceutical compositions and the methods of some aspects of the present disclosure may further include a pharmaceutically acceptable carrier, excipient or diluent. The term "pharmaceutically acceptable carrier, excipient or diluents" includes any and all solvents, dispersion media, coating agents, antigen adjuvants, stabilizers, diluents, preservatives, antibacterial and antifungal agents, isotonic agents, adsorptive delay agents, and the like. The carrier, excipient or diluent that may be included in the pharmaceutical composition may include lactose, dextrose, sucrose, sorbitol, mannitol, xylitol, maltitol, starch, glycerin, cacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate, mineral oil and the like.

As necessary, in the compositions and the methods of some aspects of the present disclosure, the C-peptide bound to the temperature-sensitive biopolymer (elastin-like polypeptide) may be used together with a biopolymer such as chitosan, poly-gamma-glutamic acid, polylactic acid, alginate and the like.

In addition, the composition and the method of some aspects of the present disclosure may be provided in the form of oral formulations, such as powders, granules, tablets, capsules, suspensions, emulsions, syrups, aerosols, etc. and formulations such as sterile injectable solutions, in accordance with typical methods. When formulated, typical diluents or excipients such as fillers, extenders, binders, wetting agents, disintegrating agents, surfactants, etc. may be used. Solid preparations for oral administration include tablets, pills, powders, granules, capsules, etc., and such solid preparations may be formulated by mixing at least one excipient, for example, starch, calcium carbonate, sucrose, lactose, gelatin, etc., with the lecithin-like emulsifier.

In addition to simple excipients, lubricants such as magnesium stearate, talc, etc. may be used. As liquid preparations for oral administration, suspension agents, solutions, emulsions, syrups, etc. may be used, and in addition to water and liquid paraffin, which are commonly used simple diluents, various excipients, for example, wetting agents, sweetening agents, fragrances, preservatives and the like, may be included. Preparations for parenteral administration include sterile aqueous solutions, non-aqueous agents, suspension agents, emulsions, and lyophilized agents. The non-aqueous agent and suspension agent may include propylene glycol, polyethylene glycol, vegetable oil such as olive oil, injectable ester such as ethyl oleate, and the like.

Some aspects of the present disclosure includes the pharmaceutical composition and the method for the prevention or treatment of diabetic complications, the method of preventing or treating diabetic complications using the same, and the use thereof.

A better understanding of some aspects of the present disclosure will be given through the following examples and experimental examples. However, these examples and experimental examples are set forth to illustrate the present invention, and the present invention is not limited to the examples and experimental examples, and may be variously modified and altered.

Experimental Example 1: Construction of Plasmids for K8 and K9-C-Peptide Production Synthetic genes for synthesizing K1-C-peptide and K1 [(VPGVG)$_{11}$(VPGKG)$_{1}$(VPGVG)$_{1}$] ELP containing a cleavable linker sequence DPNYPRGH were synthesized and bound to a pBSC (KS+) vector.

Using recursive directional ligation, as shown in FIG. 1A, a gene encoding ELP composed of eight repeating units of K1 [(VPGVG)$_{11}$(VPGKG)$_{1}$(VPGVG)$_{1}$] was produced. The gene encoding K8 [(VPGVG)$_{11}$(VPGKG)$_{1}$(VPGVG)$_{1}$]$_{8}$ was fused to the gene encoding K1-C-peptide at the 5'-end. The produced K9-C-peptide gene was inserted into a pET25b+ vector for polypeptide expression. All completed constructs confirmed the inserted sequences via DNA sequencing.

Experimental Example 2: Peptide Expression and Purification

With reference to FIG. 1B, in order to prepare K8 and K9-C-peptide, an expression vector encoding K8 and K9-C-peptide was transformed into an *E. coli* BL21 strain (DE3), followed by expression and inverse transition cycling (ITC).

Specifically, the transformed cells were induced with 1 mmol/L isopropyl beta-D-1-thiogalactopyranoside for 4 hr at 37° C. and then grown to an OD$_{600}$ of 0.4 to 0.6 at 37° C. The bacterial cells were collected through centrifugation at 4° C. at 9,000 rpm for 10 min, resuspended in a phosphate buffer saline [PBS; 8.1 mmol/L Na$_2$HPO$_4$, 1.2 mmol/L KH$_2$PO$_4$, 138 mmol/L NaCl, 2.7 mmol/L KCl (pH 8.0)], and sonicated 30 times on ice for 10 sec each. DNA and an insoluble fraction were precipitated through centrifugation at 18,000 g for 15 min at 4° C. after 10% polyethyleneimine culture on ice for 30 min. NaCl was added to a soluble fraction (final concentration of 3 mol/L) and cultured at 50° C. for 10 min. The cloudy suspension was centrifuged at 18,000 g for 15 min at 50° C. (hot spin). The supernatant was removed and the pellet was suspended in ice-cold PBS. The resulting solution was centrifuged at 18,000 g for 10 min at 4° C. and the supernatant was stored (cold spin). The ITC process was repeated once more to afford a purified product. The resulting supernatant was dialyzed against milli-Q water for 24 hr and lyophilized.

Figure 1C:
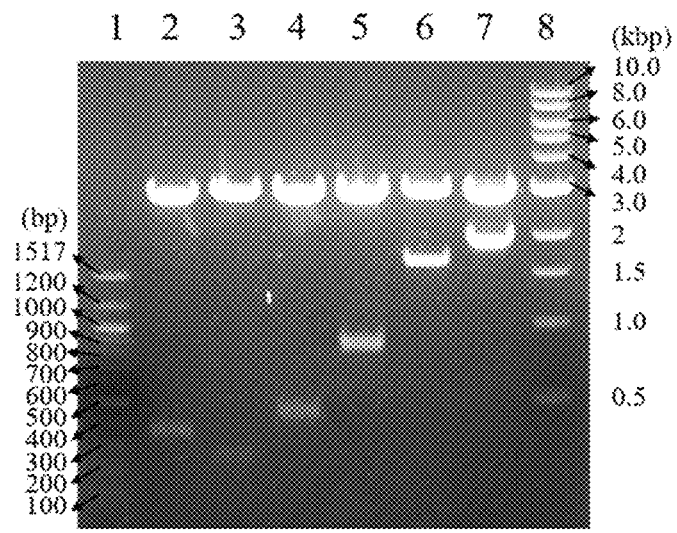

The genes obtained through the ITC process (K1, K2, K4 and K8) and the genes obtained by the fusion of K8 and K1-C-peptide were confirmed through agarose gel electrophoresis after double digestion by BamHI and HindIII (FIG. 1C). The K8 and K9-C-peptide gene sequences were confirmed through DNA sequencing.

Experimental Example 3: In-Vitro Characterization of K9-C-Peptide

In order to confirm the production and purification of K9-C-peptide, a sample collected from each ITC process was loaded on a 10% polyacrylamide gel. After electrophoresis, the gel was stained with Coomassie blue dye and imaged using a ChemiDoc™ scanner.

In order to characterize the inverse transition temperature of K9-C-peptide, the turbidity of a 2.5-100 mmol/L K9-C-peptide solution in PBS was monitored at a wavelength of 350 nm as a function of temperature at a heating rate of 1° C./min using a SpectraMax M5 Multi-Mode microplate reader (Molecular Devices, Sunnyvale, Calif.).

Figure 2A:
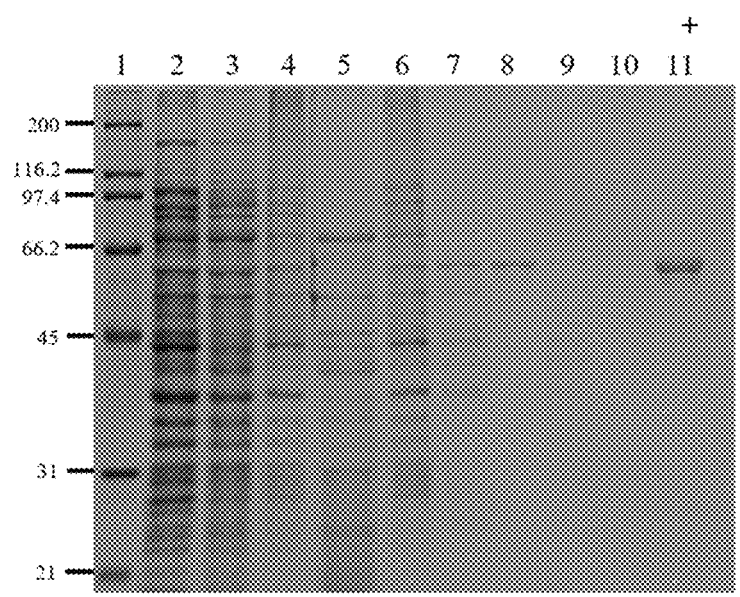
FIGS. 2A, 2B and 2C show the characteristics of K9-C-peptide in Experimental Example 3 according to an embodiment of the present disclosure.

K8 and K9-C-peptide were purified from *E. coli* using ITC. Here, the yield was 10 mg per liter of a culture broth. SDS-PAGE was used to determine the purity and molecular weight of K9-C-peptide (FIG. 2A). The samples that were maintained throughout the ITC process were visualized on SDS-PAGE gel stained with Coomassie blue, in which the 60 kDa band protein was identified as K9-C-peptide with an estimated molecular weight of 53 kDa. Western blot analysis showed that the 60 kDa band was composed of C-peptide. The results showed that K9-C-peptide was successfully purified by ITC and two ITC process cycles were sufficient to purify K9-C-peptide.

Figure 2B:
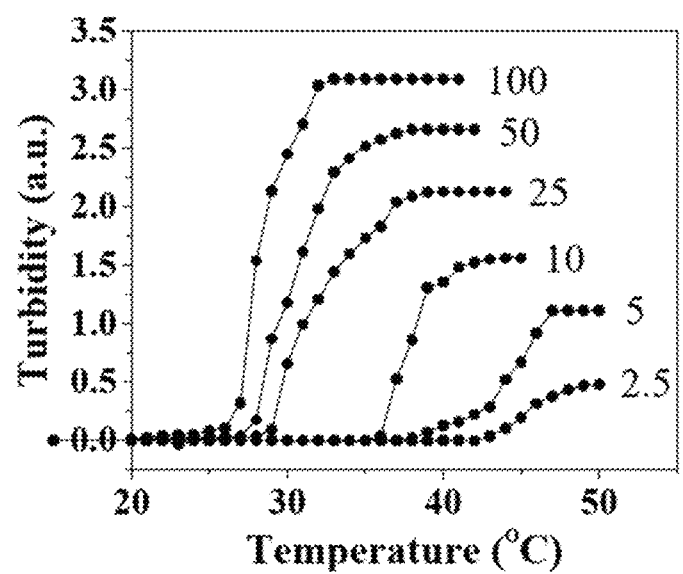
Figure 2C:
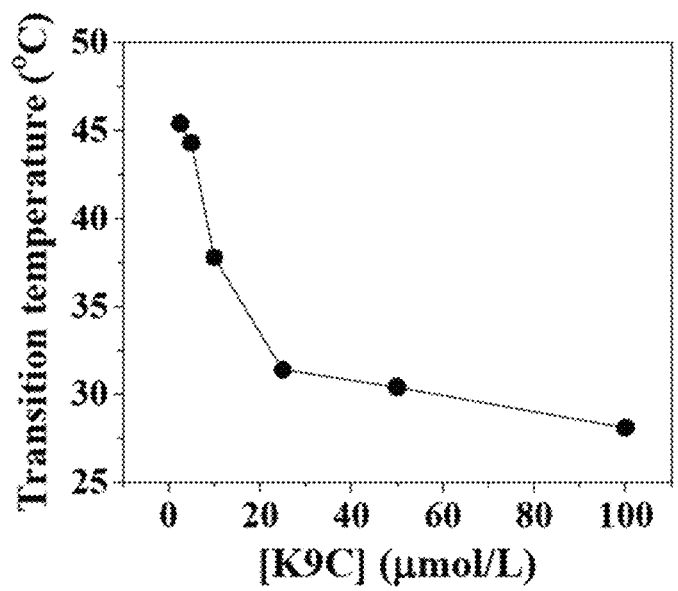

The thermal reaction of K9-C-peptide was observed by measuring the turbidity of the K9-C-peptide solution (in the range of 2.5 micromoles/L to 100 micromoles/L as a function of temperature). The turbidity of the K9-C-peptide solution increased in a temperature-dependent manner, indicating that coacervate was produced by the sol-gel transition (FIG. 2B). The transition temperature of the K9-C-peptide solution decreased from 45.4° C. to 28.1° C. in a concentration-dependent manner (FIG. 2C). These results show that the present inventors have successfully produced K9-C-peptide composed of C-peptide and 9 ELP unit repeats and that the conjugates can be used as injectable stores of C-peptide.

Experimental Example 4: Conjugation of K9-C-Peptide with Cy3-NHS Ester

K9-C-peptide was labeled with Cy3 NHS-ester.

Specifically, 1 ml of 20 mg/ml K9-C-peptide solution in a 100 mmol/L bicarbonate buffer (pH 8.3) was mixed with 13 microliters of 5 mg/ml Cy3 mono NHS-ester in 10% dimethyl sulfoxide and cultured on ice for 2 hr. In order to stop the reaction, 50 microliters of 1 mol/L Tris-HCl (pH 8.0) was added to the reaction solution. The reaction mixture was loaded in a 1.5 ml Sephadex G-25 column, and Cy3-conjugated K9-C-peptide was eluted through centrifugation at 1050×g for 3 min.

Experimental Example 5: On-Chip Degradation Profiling of K9-C-Peptide Hydrogel An amine-modified glass slide was manufactured as follows.

A glass slide (75×25 mm) was cleaned with a $H_2O_2$/$NH_4OH$/$H_2O$ (1:1:5, v/v) solution, and 1.5% (v/v) 3-aminopropyltrimethoxysilane was immersed in 95% ethanol for 2 hr and baked overnight at 110° C. A well-type amine array was manufactured by mounting a polydimethylsiloxane gasket on the amine-modified glass slide.

Enzymatic degradation profiling of K9-C-peptide by four cleavage enzymes including collagenase-2, elastase-2, pepsin and trypsin was performed as follows.

A 10 mg/ml aliquot of Cy3-conjugated K9-C-peptide was applied to the well-type amine array at 40° C. for 2 hr to thus form a hydrogel. In the array, collagenase-2 was cultured in buffer A (50 mmol/L Tris-HCl, 150 mmol/L NaCl, 5 mmol/L $CaCl_2$), 0.2 mmol/L $NaN_3$, and 0.002% Brij-35, pH 7.6), elastase-2 was cultured in buffer B (100 mmol/L Tris-HCl and 100 mmol/L NaCl, pH 7.5), pepsin was cultured in buffer C (10 mmol/L HCl, pH 2.0), and trypsin was cultured in buffer D (50 mmol/L Tris-HCl, 20 mmol/L $CaCl_2$), and 0.02% Tween-20, pH 8.1) at the indicated concentrations at 37° C. for 2 hr.

The array was rinsed with 0.1% Tween-20-containing Tris-buffer saline [TBS; 50 mmol/L Tris-HCl (pH 7.5) and 140 mmol/L NaCl] for 10 min, rinsed with Milli-Q water for 5 min, dried in air, and analyzed using a confocal microscope with a motorized sample stage.

The amount of K9-C-peptide remaining on the array surface was calculated using a standard curve, which was plotted by sigmoidal fit using the Origin program as follows.

$$x = \log x_0 - \left(\log\left(\frac{A_2 - A_1}{y - A_1} - 1\right)\middle/ P\right) \quad (1)$$

In Equation (1), x represents the concentration of K9-C-peptide, xo represents the concentration of K9-C-peptide at half the maximum fluorescence intensity, and $A_1$ and A2 represent upper and lower asymptotes, respectively. Also, y represents sample fluorescence intensity and P represents power. Then, using GraphPad PRISM8 (GraphPad Software; San Diego, Calif.), the half-maximum-effective concentration ($EC_{50}$) for the cleavage enzyme was calculated using the following modified Langmuir isotherm.

$$F_{obs} = (F_{max} \times [\text{enzyme}]/EC_{50} + [\text{enzyme}]) + \text{background} \quad (2)$$

In Equation (2), $F_{obs}$ is the fluorescence intensity of the triple spot, $F_{max}$ is the maximum fluorescence in the dark, [enzyme] is the enzyme concentration, and $EC_{50}$ is the apparent half-maximum-effective concentration.

The enzyme concentration of each protease is represented in U/ml as follows: one unit of collagenase-2 releases 1 micromole of L-leucine from collagen in 5 hr (pH 7.5 at 37° C.), one unit of elastase-2 hydrolyzes 1 mmol of MeO-Suc-APV-pNA per min (pH 7.5 at 25° C.), one unit of pepsin releases an amount of Tyr to thus cause an increase in absorbance of 0.001 per min at 280 nm (pH 2 at 37° C.), and one unit of trypsin produces an increase in absorbance of 0.001 per min at 253 nm using benzoyl L-arginine ethyl ester (pH 7.6 at 25° C.).

Figure 3A:
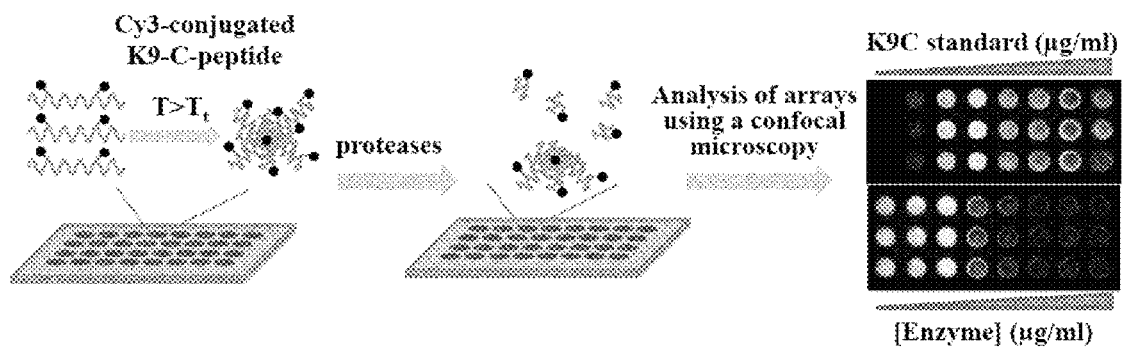
FIGS. 3A to 3E and FIGS. 4A to 4B show the release pattern of C-peptide from K9-C-peptide in Experimental Example 4 according to an embodiment of the present disclosure.
Figure 3B:
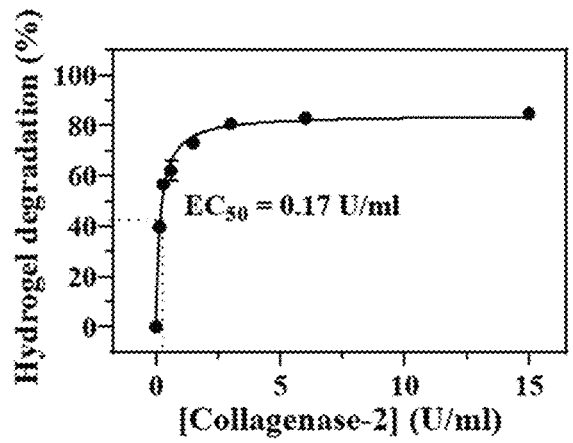
Figure 3C:
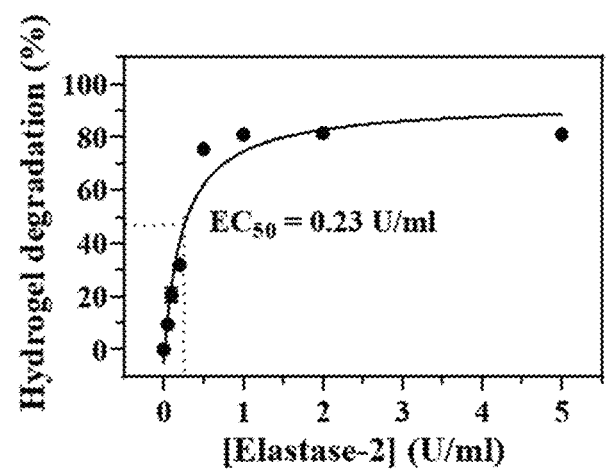
Figure 3D:
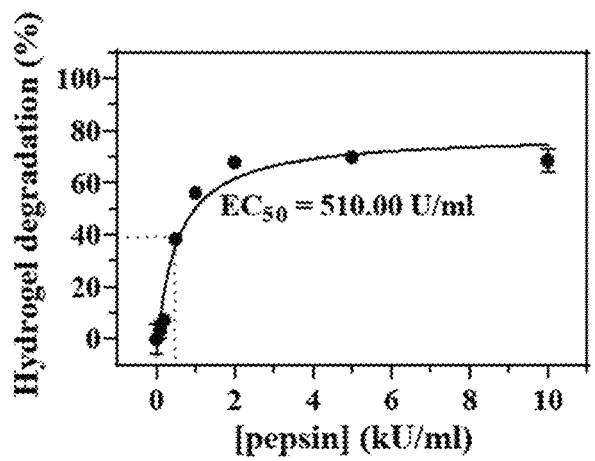
Figure 3E:
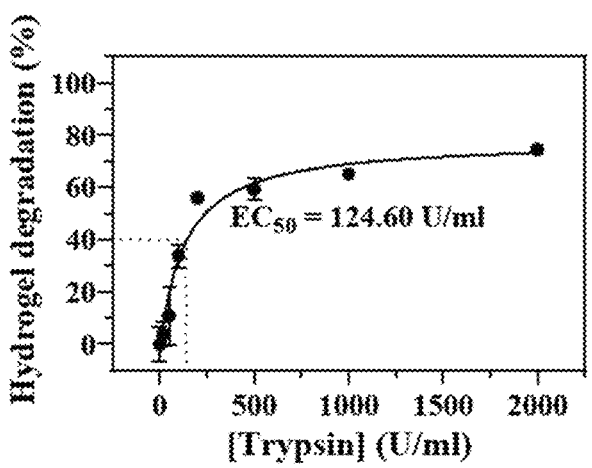

Degradation of the K9-C-peptide hydrogel was observed using an on-chip degradation assay. This is because this assay allows for ultrafast analysis using a small volume of sample. In order to visualize and quantify the degradation of K9-C-peptide by proteases, K9-C-peptide was covalently conjugated with Cy3 NHS-ester, and the Cy3-conjugated K9-C-peptide hydrogel array was manufactured using a well-type amine array and then incubated with four proteases, namely collagenase-2, elastase-2, pepsin and trypsin, at the indicated concentrations (FIG. 3A).

$EC_{50}$ values for individual enzymes were determined by graphing the degradation rate based on the amount of Cy3-conjugated K9-C-peptide fragment separated from the spot on the array, versus the protease concentration. All four enzymes increased K9-C-peptide degradation in an enzyme-concentration-dependent manner (FIGS. 3B to 3E). $EC_{50}$ values for the four enzymes were 0.17 U/ml, 0.23 U/ml, 510.00 U/ml and 124.60 U/ml, respectively. These results demonstrate that collagenase-2 and elastase-2 cleave K9-C-peptide more efficiently than pepsin and trypsin.

Figure 4A:
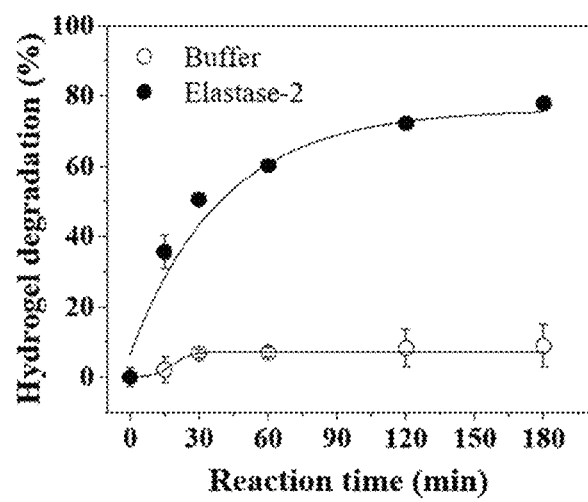
Figure 4B:
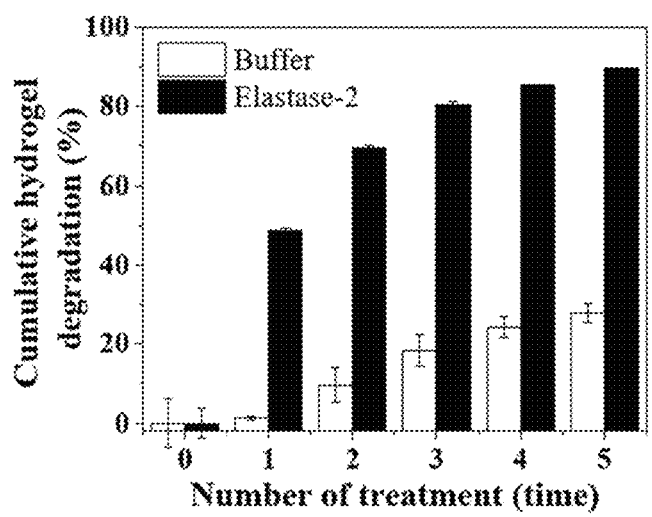

In order to simulate the release of C-peptide by hydrogel degradation in the presence of protease, the present inventors observed the time-dependent degradation of Cy3-conjugated K9-C-peptide hydrogel using an on-chip degradation assay by applying elastase-2 to the hydrogel array for a designated time. The degradation of K9-C-peptide hydrogel by elastase-2 increased in a time-dependent manner. The highest degradation rate was 72.3% at 120 min, and a degradation rate of less than 10% was achieved with the reaction buffer alone (FIG. 4A). Then, the present inventors confirmed that Cy3-conjugated K9-C-peptide hydrogel was gradually degraded by repeated treatment of elastase-2, which was performed every 30 min. The results showed that 48.6+/−0.8% of the hydrogel was degraded after the first treatment, and the degradation rate of the hydrogel increased with the number of treatment processes, but the maximum degradation rate (89.7+/−0.2%) was achieved after the fifth treatment (FIG. 4B). In the absence of elastase-2, the degradation rate of K9-C-peptide hydrogel increased from 1.3+/−0.6% (i.e. after the first treatment) to 27.9+/−2.5% (after the fifth treatment) depending on the number of buffer treatment processes, indicating that repeated rinsing with detergent-containing buffer caused partial degradation of the hydrogel. These results suggest that C-peptide bound to the ELP hydrogel can be released by blood-circulating proteases, including elastase-2.

Experimental Example 6: Cell Culture and Treatment

Human aortic endothelial cells (HAECs) purchased from PromoCell (Heidelberg, Germany) were cultured in an M19 medium containing 20% FBS, 3 ng/mL bFGF, 5 U/mL heparin, 100 U/mL penicillin and 100 mg/mL streptomycin in a 2% gelatin-coated medium.

For the experiments described below, the HRECs were incubated for 6 hr in a low-serum medium containing 2% FBS, 0.1 ng/ml bFGF and antibiotic, and were then treated with 30 mmol/L D-glucose.

Experimental Example 7: Measurement of Intracellular ROS and TGase Activity Levels Intracellular ROS levels were measured using 2',7'-dichlorodihydrofluorescein diacetate (H2DCFDA) (ThermoFisher Scientific, Waltham, Mass.). HAECs were treated with human C-peptide, K8 and K9-C-peptide at various concentrations (0 nM, 0.5 nM, 1.0 nM, 1.5 nM, and 2.0 nM), incubated for 30 min, and treated with 10 mmol/L H2DCFDA for 10 min. The labeled cells were analyzed using a confocal microscope (K1-Fluo). Single-cell fluorescence intensity was measured for 30 randomly selected cells/experiment. Intracellular ROS was measured by comparing the fluorescence intensity of the treated cells with that of control cells.

Intracellular TGase activity was measured by introducing incorporated 5-(biotinamido)pentylamine (BAPA) into the cells. HAECs were pretreated with human C-peptide, K8 and K9-C-peptide at various concentrations (0 nM, 0.5 nM, 1.0 nM, 1.5 nM, and 2.0 nM) for 30 min, and were then treated with 1 mmol/L BAPA for 60 min. Incorporation of BAPA into TGase2-mediated cells, cell fixation and permeation, and irradiation with FITC-conjugated streptavidin for 1 hr (1:200; MilliporeSigma, Burlington, Mass., USA) were performed. The fluorescence intensity of the stained cells was measured through confocal microscopy (K1-fluo) for 30 randomly selected cells/experiment.

Figure 5A:
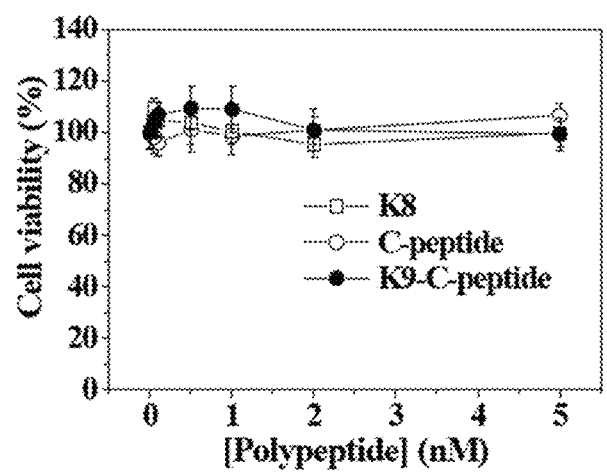
FIGS. 5A to 5E, respectively, show the results of changes in concentration of reactive oxygen species and TGase activity in Experimental Example 7 and of evaluation of cytotoxicity in Experimental Example 8.
Figure 5B:
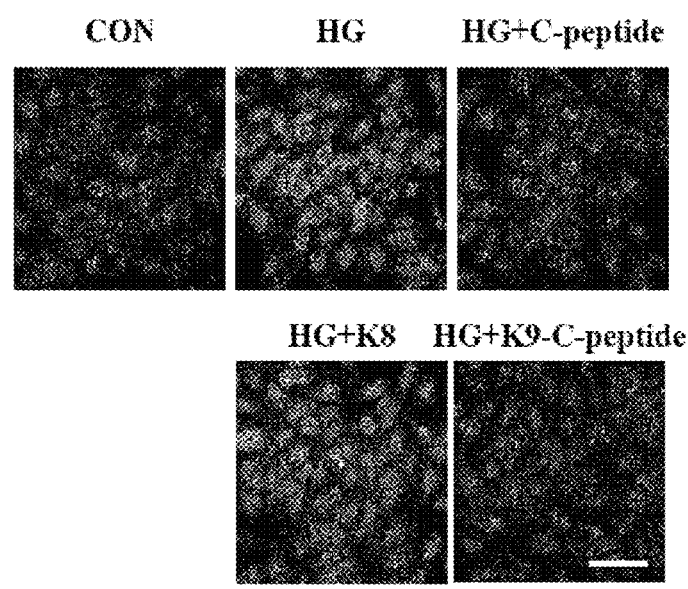
Figure 5C:
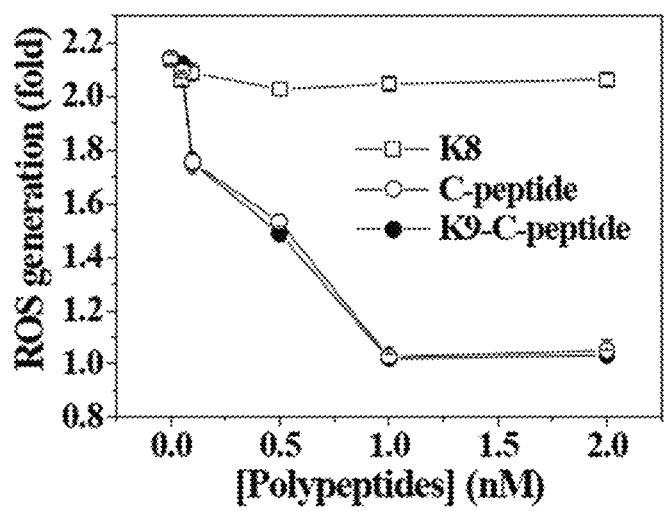
Figure 5D:
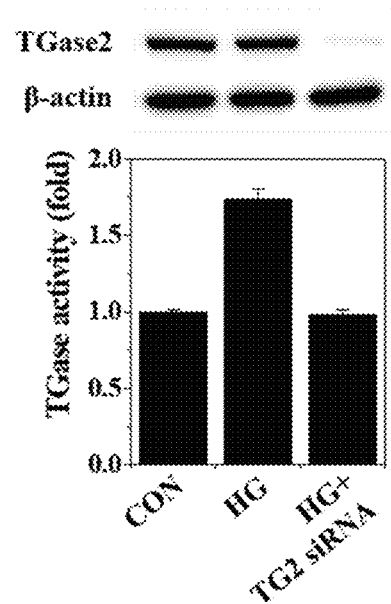
Figure 5E:
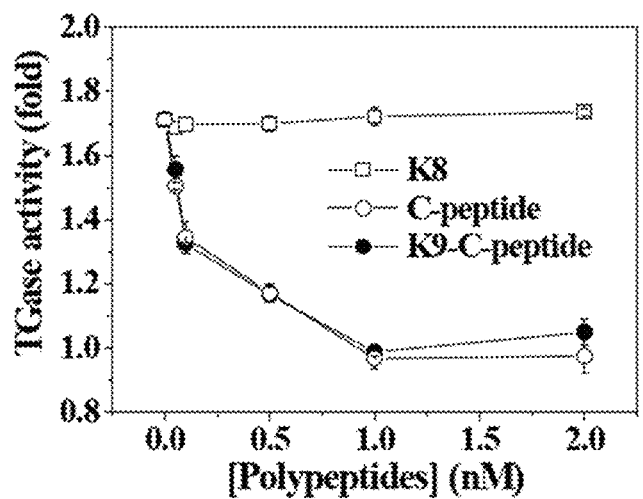

Hyperglycemia increased intracellular ROS levels by approximately 2.1 times, which was prevented by K9-C-peptide treatment in a concentration-dependent manner, with a maximum effect achieved at 1 nM (FIGS. 5B and 5C). Human C-peptide showed a hyperglycemia-induced ROS generation inhibitory effect similar to that of K9-C-peptide, but K8 did not show any inhibitory effect. The present inventors then studied the effects of K9-C-peptide and human C-peptide on hyperglycemia-induced TGase2 activation in HAECs. Hyperglycemia increased in-situ TGase activity by approximately 1.7 times, which was inhibited by transfection of TGM2-specific siRNA (FIG. 5D). TGM-2 siRNA inhibited TGase2 protein expression, indicating that TGase2, which is a member of the TGase family, overwhelmingly contributes to hyperglycemia-induced TGase activation in HAECs. Both K9-C-peptide and human C-peptide inhibited hyperglycemia-induced TGase2 activation in a similar manner (in a concentration-dependent manner). Here, the maximum effect was achieved at 1 nM, whereas K8 had no effect (FIG. 5E).

Experimental Example 8: Evaluation of Cytotoxicity of C-Peptide Derivatives

The cytotoxicity of C-peptide derivatives was evaluated as follows.

HAECs were cultured in a 24-well plate, and treated with human C-peptide, K8 and K9-C-peptide at concentrations of 0 nM, 1 nM, 2 nM, 3 nM and 5 nM for 24 hr. After the medium was replaced with a fresh medium, 200 microliters of 1 mg/ml 3-(4,5-dimethylthiazolyl-2)-2,5-diphenyltetrazolium bromide solution was added to each well and cultured for 4 hr. The resulting formazan crystals were dissolved in dimethyl sulfoxide, and the absorbance of each well at 570 nm was observed.

With reference to FIG. 5A, K9-C-peptide did not show any cytotoxicity at concentrations ranging from 1 nmol/L to 5 nmol/L. Human C-peptide and K8, that is, a negative control biopolymer of K9-C-peptide without C-peptide, also showed no cytotoxicity. Therefore, K9-C-peptide is biocompatible and can be used to study the effect of K9-C-peptide on hyperglycemia-induced intracellular phenomena in HAECs.

Experimental Example 9: Measurement of Apoptosis

Apoptotic cells were measured through a terminal deoxynucleotidyl transferase dUTP nick end labeling (TUNEL) assay using an APO-BrdU TUNEL assay kit (BD Bioscience; San Jose, Calif.).

Specifically, the cells were fixed for 20 min with 1% (w/v) paraformaldehyde in PBS, and were then treated for 30 min with 70% (v/v) ethanol on ice. The fixed cells were cultured with a DNA-labeling solution containing terminal deoxynucleotidyl transferase and 5-bromo-2-deoxyuridine in a reaction buffer for 1 hr at 37° C. Subsequently, the cells were cultured with a FITC-labeled 5-bromo-2-deoxyuridine antibody for 30 min and with 1 micrograms/ml DAPI for 10 min. The mounted cells were observed using a confocal microscope (K1-Fluo).

Figure 6A:
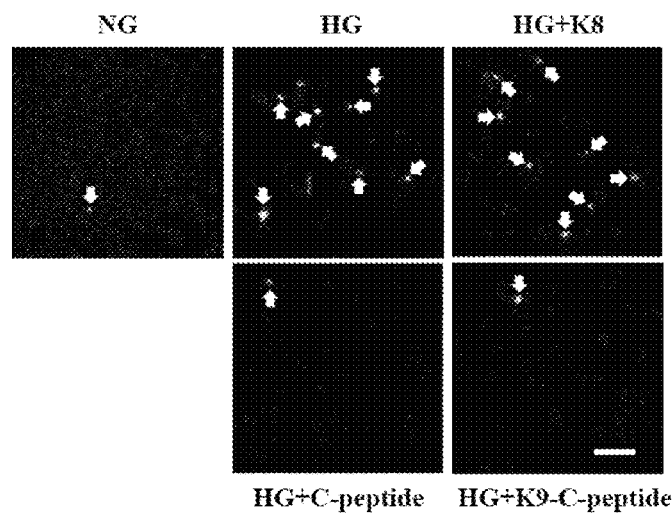
FIGS. 6A and 6B show the results of evaluation of apoptosis in Experimental Example 9.
Figure 6B:
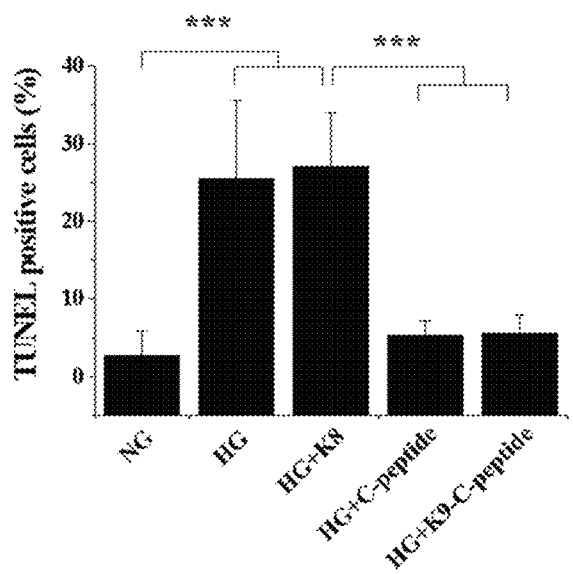

Hyperglycemia increased the number of TUNEL-positive cells, but this result was inhibited both by K9-C-peptide and by human C-peptide, but not by K8 (FIGS. 6A and 6B).

Experimental Example 10: Distribution and Retention of K9-C-Peptide in Mouse Eyes In order to evaluate the retention of K9-C-peptide when injecting K9-C-peptide into the eyes, mouse eyes were injected with 10 micrograms of K9-C-peptide with fluorescence (FITC) and PBS as a control.

Figure 7:
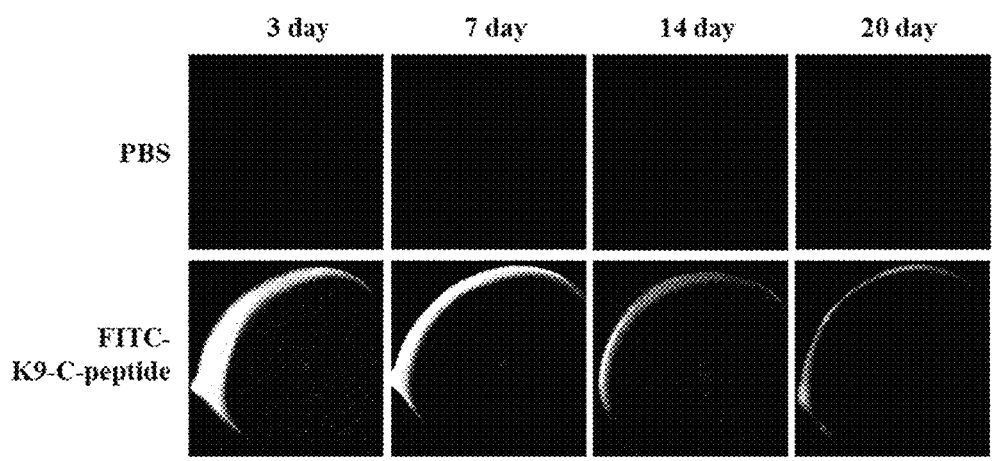
FIG. 7 shows the results of distribution of K9-C-peptide in mouse eyes in Experimental Example 10.

With reference to FIG. 7, injecting FITC-K9-C-peptide into the mouse eyes confirmed the presence of K9-C-peptide for about 20 days.

From this, it is expected that C-peptide, having a therapeutic effect, can be released from K9-C-peptide for 20 days upon a single injection of K9-C-peptide.

Experimental Example 11: Effect of K9-C-Peptide on Inhibiting Hyperglycemia-Induced Vascular Leakage in Diabetic Mouse Retina In order to evaluate the effect of 9-C-peptide on inhibiting vascular leakage in the diabetic mouse retina, 10 micrograms of K9-C-peptide and PBS, 10 micrograms of K8, and 6 ng of C-peptide were injected into the mouse retina.

Figure 8:
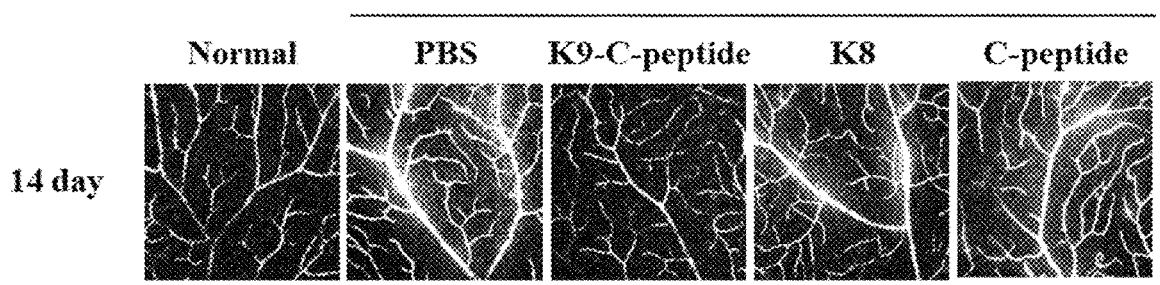
FIG. 8 shows the results of effects of K9-C-peptide on inhibiting vascular leakage caused by diabetes in the diabetic mouse retina in Experimental Example 11.

With reference to FIG. 8, vascular leakage was confirmed in the diabetic mouse retina, and the mouse eyes were injected with K9-C-peptide and PBS, K8, (9-C-peptide negative control), and C-peptide. Based on the results of observation after 14 days, K8 and PBS did not affect vascular leakage, and C-peptide alone showed a therapeutic effect for about one day after injection, but not thereafter. On the other hand, 14 days after injection of K9-C-peptide, the effect thereof on inhibiting vascular leakage was confirmed.

Therefore, K9-C-peptide showed a long-term inhibitory effect on vascular leakage compared to the C-peptide alone, indicating that K9-C-peptide remained in the eyes for 14 days, resulting in continuous release of C-peptide from K9-C-peptide to thus exhibit a therapeutic effect.

Experimental Example 12: Evaluation of Effect of K9-C-Peptide on Inhibiting Diabetic Kidney Disease 6-week-old male C57BL/6 mice were prepared and divided into a normal mouse group (hereinafter referred to as a normal group), a diabetic mouse group (hereinafter referred to as a diabetic group) and a group in which K9-C-peptide was injected into diabetic mice (hereinafter referred to as a K9C treatment group). Here, in the diabetic group, a diabetic model was made by injecting the abdominal cavity with 150 mg/kg of streptozotocin (STZ). In the K9C treatment group, the same diabetic model as the diabetic group was made, and after two weeks, subcutaneous injection with 100 mg/kg K9-C-peptide was carried out.

After 24 hr, whether K9-C-peptide had an effect on inhibiting renal vascular leakage caused by hyperglycemia was evaluated.

Based on the results of measurement of the mouse weight of each group, the mouse weight was 23.7+/−0.6 g in the normal group, was 19.9+/−0.8 g in the diabetic group, and was 19.1+/−0.7 g in the K9C treatment group. Based on the results of measurement of the mouse blood sugar level of each group, the mouse blood sugar level was 122.5+/−4.5 mg/dL in the normal group, was 504.0+/−10.0 mg/dL in the diabetic group, and was 505.3+/−8.2 mg/dL in the K9C treatment group.

In order to observe renal vascular leakage, 1.25 mg of FITC-dextran was injected into the right ventricle of the mouse of each group and circulated for 5 min, and the kidneys were dissected, fixed and embedded in an OCT compound. Kidney tissues were observed through confocal microscopy after cryosection followed by staining with DAPI.

Figure 9A:
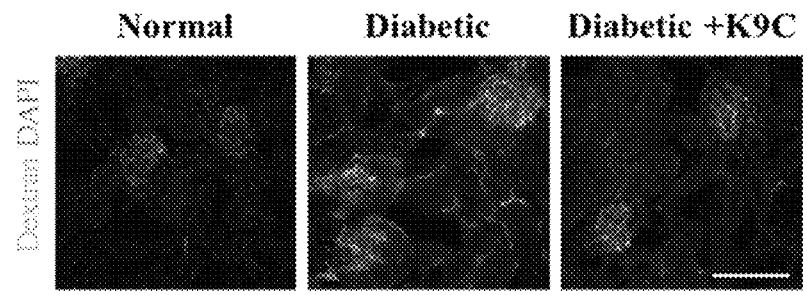
FIGS. 9A and 9B show the effects of K9-C-peptide on inhibiting renal vascular leakage in diabetic mice in Experimental Example 12.

FIG. 9A shows representative renal vascular leakage images of individual groups.

Additionally, vascular leakage was quantitatively analyzed by measuring the fluorescence intensity of FITC-dextran in the mouse kidneys of each group. The results thereof are shown in FIG. 9B (normal group, diabetic group and K9C treatment group; n=4).

Figure 9B:
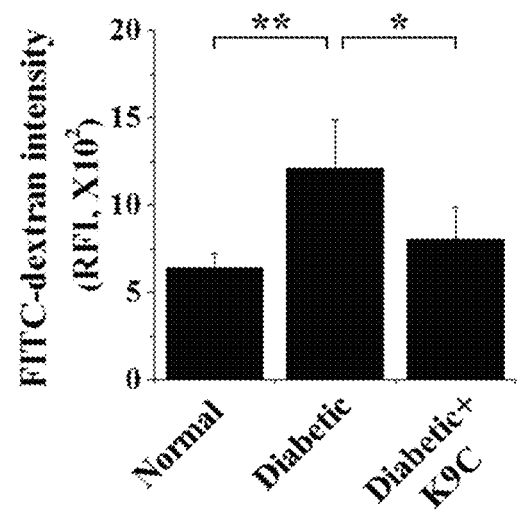

With reference to FIG. 9B, more vascular leakage of FITC-dextran was observed in the diabetic group compared to the normal group. It was confirmed that vascular leakage was suppressed in the KC9 treatment group.

In conclusion, it was experimentally confirmed that renal vascular leakage was suppressed by K9-C-peptide administration and that nephropathy of the diabetic mice was effectively inhibited by K9-C-peptide.

Experimental Example 13: Evaluation of Effect of K9-C-Peptide on Inhibiting Diabetic Lung Disease 6-week-old male C57BL/6 mice were prepared and divided into a normal mouse group (hereinafter referred to as a normal group), a diabetic mouse group (hereinafter referred to as a diabetic group) and a group in which K9-C-peptide was injected into diabetic mice (hereinafter referred to as a K9C treatment group). Here, in the diabetic group, a diabetic model was made by injecting the abdominal cavity with 150 mg/kg of streptozotocin (STZ). In the K9C treatment group, the same diabetic model as the diabetic group was made, and after two weeks, subcutaneous injection with 100 mg/kg K9-C-peptide was carried out. After 24 hr, whether K9-C-peptide had an effect on inhibiting lung vascular leakage caused by hyperglycemia was evaluated.

Based on the results of measurement of the mouse weight of each group, the mouse weight was 23.7+/−0.6 g in the normal group, was 19.9+/−0.8 g in the diabetic group, and was 19.1+/−0.7 g in the K9C treatment group. Also, based on the results of measurement of the mouse blood sugar level of each group, the mouse blood sugar level was 122.5+/−4.5 mg/dL in the normal group, was 504.0+/−10.0 mg/dL in the diabetic group, and was 505.3+/−8.2 mg/dL in the K9C treatment group.

In order to observe the lung vascular leakage, 1.25 mg of FITC-dextran was injected into the right ventricle of each mouse and circulated for 5 min, and the lungs were dissected, fixed and embedded in an OCT compound. Lung tissues were observed through confocal microscopy after cryosection followed by staining with DAPI.

Figure 10A:
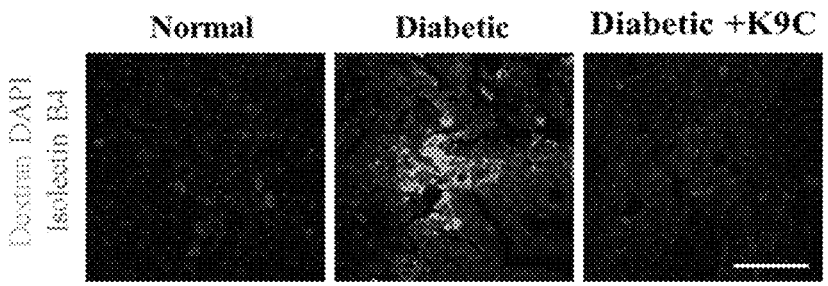
FIGS. 10A and 10B show the effects of K9-C-peptide on inhibiting lung vascular leakage in diabetic mice in Experimental Example 13.

FIG. 10A shows representative lung vascular leakage images of individual groups.

Moreover, vascular leakage was quantitatively analyzed by measuring the fluorescence intensity of FITC-dextran in the mouse lungs of each group. The results thereof are shown in FIG. 10B (normal group and diabetic group; n=4, K9C treatment group; n=6).

Figure 10B:
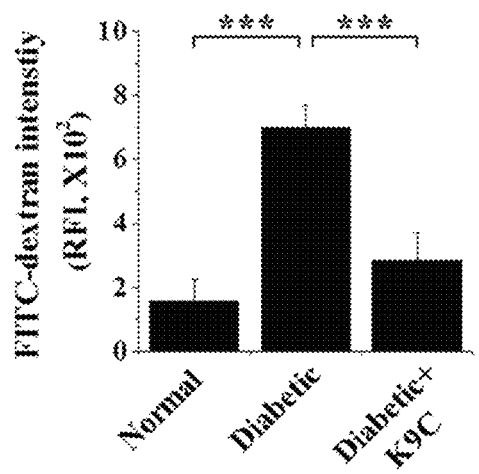

With reference to FIG. 10B, more vascular leakage of FITC-dextran was observed in the diabetic group compared to the normal group. It was confirmed that vascular leakage was suppressed in the KC9 treatment group.

In conclusion, it was experimentally confirmed that lung vascular leakage was suppressed by K9-C-peptide administration and that the lung disease of the diabetic mice was effectively inhibited by K9-C-peptide.

Experimental Example 14: Evaluation of Effect of K9-C-Peptide on Inhibiting Diabetic Cardiovascular Disease 6-week-old male C57BL/6 mice were prepared and divided into a normal mouse group (hereinafter referred to as a normal group), a diabetic mouse group (hereinafter referred to as a diabetic group) and a group in which K9-C-peptide was injected into diabetic mice (hereinafter referred to as a K9C treatment group). Here, in the diabetic group, a diabetic model was made by injecting the abdominal cavity with 150 mg/kg of streptozotocin (STZ). In the K9C treatment group, the same diabetic model as the diabetic group was made, and after two weeks, subcutaneous injection with 100 mg/kg K9-C-peptide was carried out. After 2 weeks, whether K9-C-peptide had an effect on aortic endothelial cell death caused by hyperglycemia was evaluated.

Based on the results of measurement of the mouse weight of each group, the mouse weight was 25.9+/−0.9 g in the normal group, was 20.2+/−0.3 g in the diabetic group, and was 21.3+/−0.6 g in the K9C treatment group. Also, based on the results of measurement of the mouse blood sugar level of each group, the mouse blood sugar level was 128.5+/−9.5 mg/dL in the normal group, was 553.0+/−39.0 mg/dL in the diabetic group, and was 548.0+/−14.7 mg/dL in the K9C treatment group.

In order to observe the aortic endothelial cell death effect, the abdominal cavity of each mouse was incised, and the aorta was separated, cut longitudinally, expanded, fixed with 1% paraformaldehyde for 15 min and then further fixed with 70% ethanol for 30 min. Cells in which apoptosis occurred were stained using an APO-BrdU TUNEL Assay Kit, and nuclei were stained using DAPI, followed by observation through confocal microscopy.

Figure 11A:
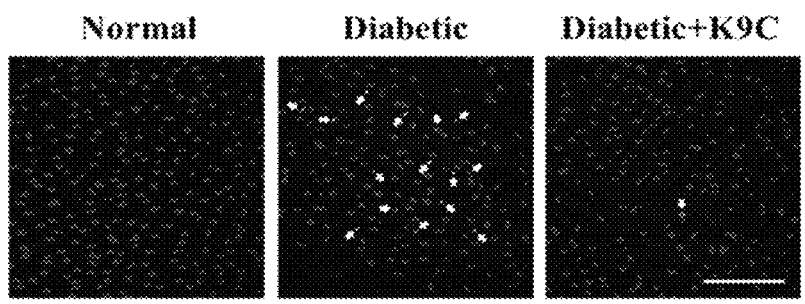
FIGS. 11A and 11B show the effects of K9-C-peptide on inhibiting endothelial cell death in the diabetic mouse aorta in Experimental Example 14.

FIG. 11A shows representative endothelial cell death images of individual groups.

Moreover, the results of apoptosis in aortic endothelial cells of the mice in each group were quantitatively analyzed through a TUNEL assay. The results thereof are shown in FIG. 11B (normal group and diabetic group; n=4, K9C treatment group; n=6).

Figure 11B:
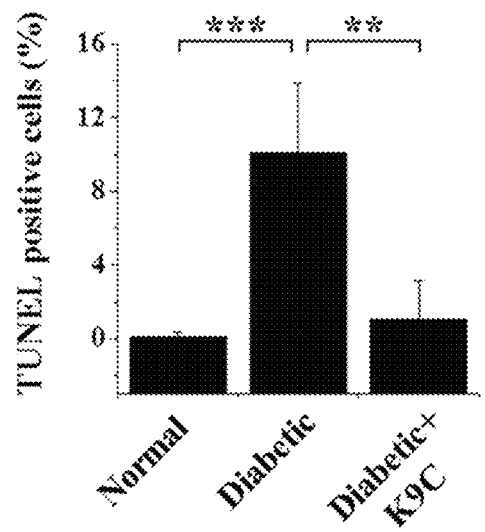

With reference to FIG. 11B, it was confirmed that endothelial cell death was increased in the diabetic group compared to the normal group and that apoptosis in the aortic endothelial cells was inhibited in the KC9 treatment group.

In conclusion, it was experimentally confirmed that the endothelial cell death induced by hyperglycemia in the aorta

Experimental Example 15: Evaluation of Effect of K9-C-Peptide on Inhibiting Diabetic Wound-Healing Delay 6-week-old male C57BL/6 mice were prepared and divided into a normal mouse group (hereinafter referred to as a normal group), a diabetic mouse group (hereinafter referred to as a diabetic group) and a group in which K9-C-peptide was injected into diabetic mice (hereinafter referred to as a K9C treatment group). Here, in the diabetic group, a diabetic model was made by injecting the abdominal cavity with 150 mg/kg of streptozotocin (STZ). In the K9C treatment group, the same diabetic model as the diabetic group was made, and after two weeks, subcutaneous injection with 100 mg/kg K9-C-peptide was carried out. After 24 hr, whether K9-C-peptide had an effect on inhibiting wound-healing delay caused by hyperglycemia was evaluated.

Based on the results of measurement of the mouse weight of each group, the mouse weight was 26.0+/−0.1 g in the normal group, was 19.9+/−0.1 g in the diabetic group, and was 19.3+/−0.4 g in the K9C treatment group. Also, based on the results of measurement of the mouse blood sugar level of each group, the mouse blood sugar level was 116.0+/−14.0 mg/dL in the normal group, was 503.5+/−4.5 mg/dL in the diabetic group, and was 505.0+/−3.0 mg/dL in the K9C treatment group.

In order to observe the wound-healing delay phenomenon, a wound 6 mm in size was made on the dorsal skin of the mouse. The wound was then photographed with a camera and the size thereof was measured using Vernier calipers.

Figure 12A:
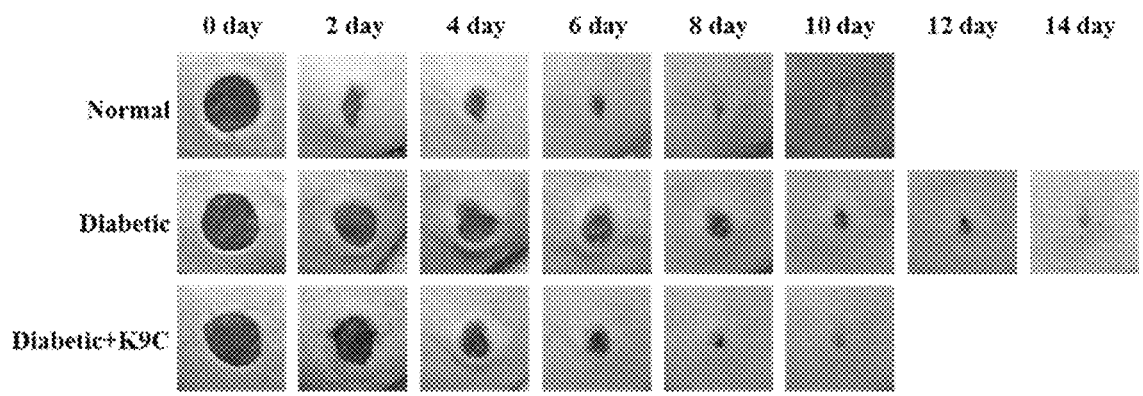
FIGS. 12A and 12B show the effects of K9-C-peptide on inhibiting wound-healing delay in diabetic mice in Experimental Example 15.

FIG. 12A shows images of representative wound sizes of individual groups.

Figure 12B:
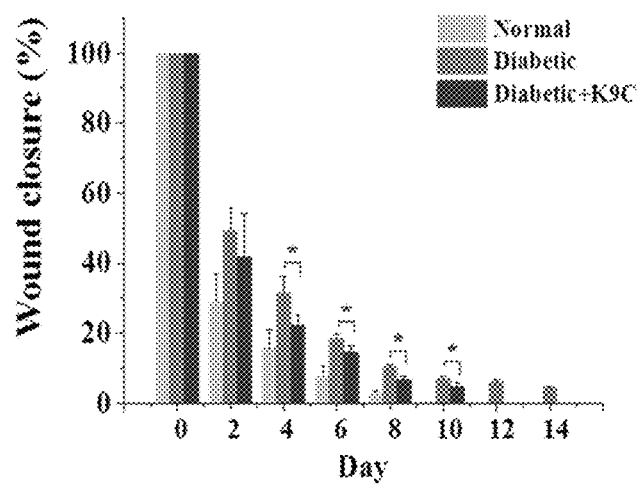

Additionally, the wound size of each group was directly measured in order to quantitatively analyze the wound-healing rate, and the results thereof are shown in FIG. 12B (normal group, diabetic group and K9C treatment group; n=4).

With reference to FIG. 12B, it was confirmed that wound healing was delayed in the diabetic group compared to the normal group and that the wound-healing delay was suppressed in the KC9 treatment group.

In conclusion, it was experimentally confirmed that the wound-healing delay induced by hyperglycemia was suppressed by K9-C-peptide administration and that wound healing in the diabetic mice was effectively promoted by K9-C-peptide.

Experimental Example 16: Evaluation of Effect of K9-C-Peptide on Inhibiting Diabetic Cancer Metastasis 6-week-old male C57BL/6 mice were prepared and divided into a normal mouse group (hereinafter referred to as a normal group), a diabetic mouse group (hereinafter referred to as a diabetic group) and a group in which K9-C-peptide was injected into diabetic mice (hereinafter referred to as a K9C treatment group). Here, in the diabetic group, a diabetic model was made by injecting the abdominal cavity with 150 mg/kg of streptozotocin (STZ). In the K9C treatment group, the same diabetic model as the diabetic group was made, and after two weeks, subcutaneous injection with 100 mg/kg K9-C-peptide was carried out. After 24 hr, B16F10 (melanoma cells) of $5\times10^5$ cells were intravenously injected into each group to thus make a cancer metastasis model, and whether K9-C-peptide had an effect on inhibiting cancer metastasis in diabetic mice was evaluated.

Based on the results of measurement of the mouse weight of each group, the mouse weight was 26.6+/−0.4 g in the normal group, was 20.4+/−0.4 g in the diabetic group, and was 20.4+/−0.4 g in the K9C treatment group. Also, based on the results of measurement of the mouse blood sugar level of each group, the mouse blood sugar level was 127.7+/−3.5 mg/dL in the normal group, was 557.8+/−7.0 mg/dL in the diabetic group, and was 543.7+/−24.8 mg/dL in the K9C treatment group.

On the other hand, in order to confirm the cancer metastasis, two weeks after intravenous injection to each group, the lungs of the mice were separated and immersed in Fekete's solution and the tissues thereof were bleached.

Figure 13A:
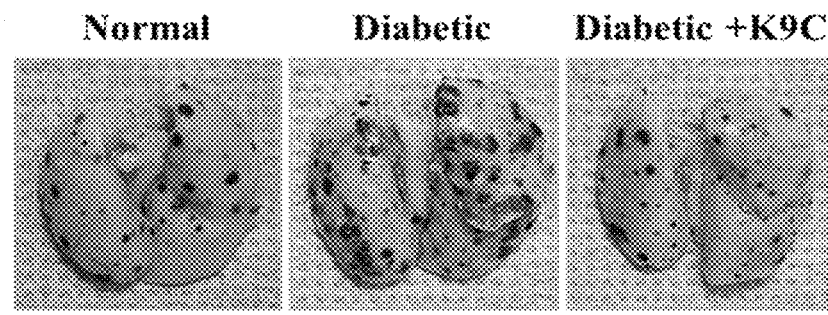
FIGS. 13A and 13B show the effects of K9-C-peptide on inhibiting cancer metastasis in diabetic mice in Experimental Example 16.

FIG. 13A shows representative cancer metastasis images of individual groups.

Figure 13B:
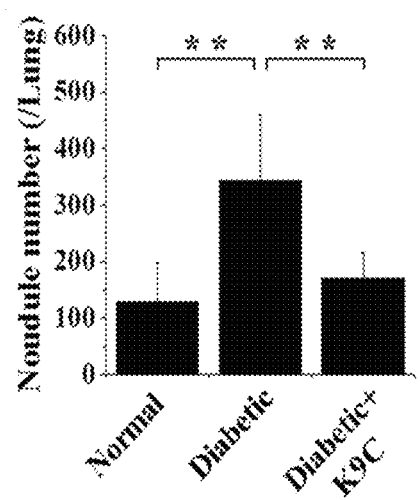

Moreover, cancer metastasis was quantitatively analyzed by counting tumor nodules occurring in the lungs using a microscope, and the results thereof are shown in FIG. 13B (normal group and diabetic group n=6, K9C treatment group; n=7).

With reference to FIG. 13B, it was confirmed that cancer metastasis was increased in the diabetic group compared to the normal group and that cancer metastasis was suppressed in the KC9 treatment group.

In conclusion, it was experimentally confirmed that cancer metastasis in the diabetic mice was suppressed by K9-C-peptide administration and that cancer metastasis in the diabetic mice was effectively inhibited by K9-C-peptide.

What is claimed is:

1. A method for treating diabetic complications comprising:
   administering to a subject with diabetes having diabetic complications a pharmaceutical composition comprising an effective amount of a C-peptide bound to an elastin-like polypeptide (ELP),
   wherein the elastin-like polypeptide comprises an amino acid sequence of SEQ ID NO: 3, and
   wherein the C-peptide comprises an amino acid sequence of SEQ ID NO: 4.

2. The method of claim 1, wherein the elastin-like polypeptide and the C-peptide are directly linked to each other or are bound by a linker.

3. The method of claim 2, wherein the linker comprises an amino acid sequence of SEQ ID NO: 5.

4. The method of claim 1, wherein the diabetic complications comprise diabetic retinopathy, diabetic stroke, diabetic cardiovascular disease, diabetic kidney disease, diabetic lung disease, diabetic peripheral neuropathy, diabetic wound-healing delay or diabetic cancer metastasis.

5. The method of claim 4, wherein the diabetic complications comprise diabetic retinopathy, diabetic lung disease, diabetic kidney disease, diabetic wound-healing delay, diabetic cancer metastasis or diabetic cardiovascular disease.

6. The method of claim 1, wherein the pharmaceutical composition inhibits an increase in intracellular reactive oxygen species (ROS) levels and transglutaminase 2 (TGase 2) activity.

7. The method of claim 1, wherein the C-peptide bound to the elastin-like polypeptide has a phase-transition behavior.

* * * * *